United States Patent [19]
Carangelo et al.

[11] Patent Number: 5,841,546
[45] Date of Patent: Nov. 24, 1998

[54] NON-CONTACT SPECTROSCOPY SYSTEM AND PROCESS

[75] Inventors: Robert M. Carangelo, Glastonbury, Conn.; Mark A. Druy, Arlington, Mass.; William A. Stevenson, Concord, Mass.; Paul J. Glatkowski, Littleton, Mass.

[73] Assignee: Foster-Miller, Inc., Waltham, Mass.

[21] Appl. No.: 609,648

[22] Filed: Mar. 1, 1996

[51] Int. Cl.⁶ .......................... G01N 21/35; G01N 21/55
[52] U.S. Cl. .............. 356/445; 250/227.23; 250/339.08; 250/339.11
[58] Field of Search ..................................... 356/445, 446; 250/339.07, 339.08, 339.11, 341.8, 227.18, 227.23

[56] References Cited

U.S. PATENT DOCUMENTS

| | | | |
|---|---|---|---|
| 3,747,755 | 7/1973 | Senturia et al. | 350/339.11 |
| 4,644,163 | 2/1987 | Selander | 356/446 X |
| 5,038,038 | 8/1991 | Weniger et al. | 250/339.11 |

*Primary Examiner*—Vincent P. McGraw
*Attorney, Agent, or Firm*—Fish & Richardson P.C.

[57] ABSTRACT

A non-contact spectroscopy system includes scanning head structure with transmitting optics for focusing radiation onto the surface of material to be analyzed, and receiving optics for collecting radiation reflected from the surface of the material and directing the reflected radiation onto optic fiber structure for transmission to spectroscopic analyzer structure.

19 Claims, 3 Drawing Sheets

FIG. 1
FIG. 2
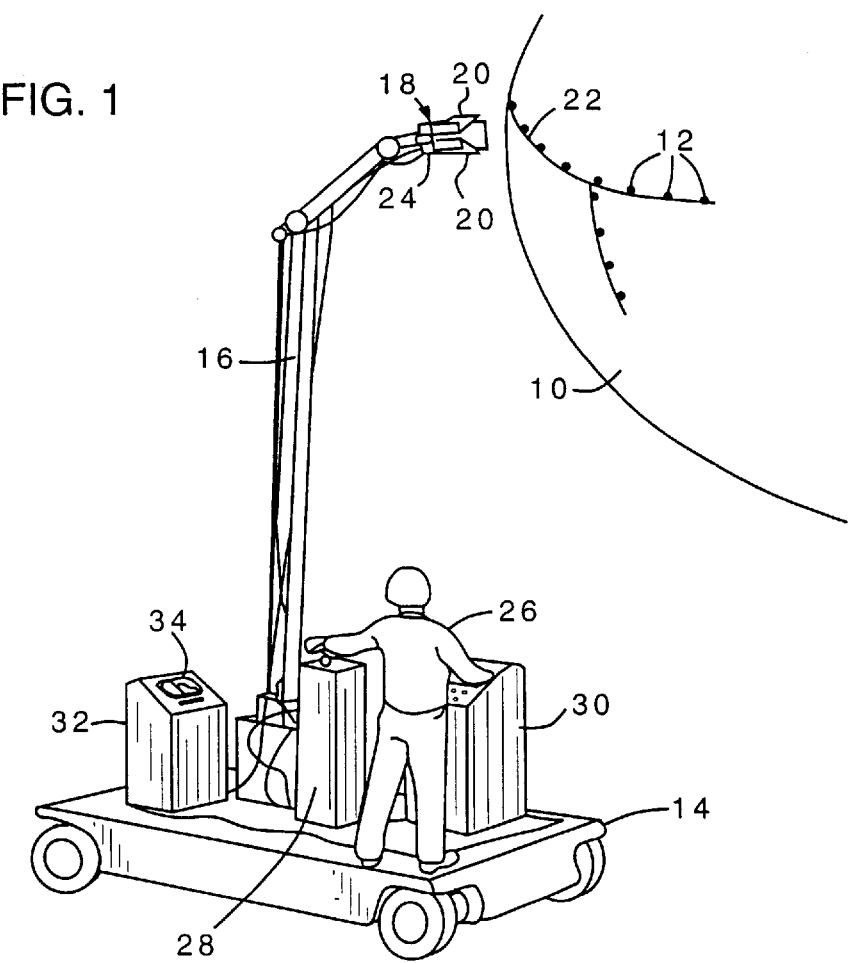
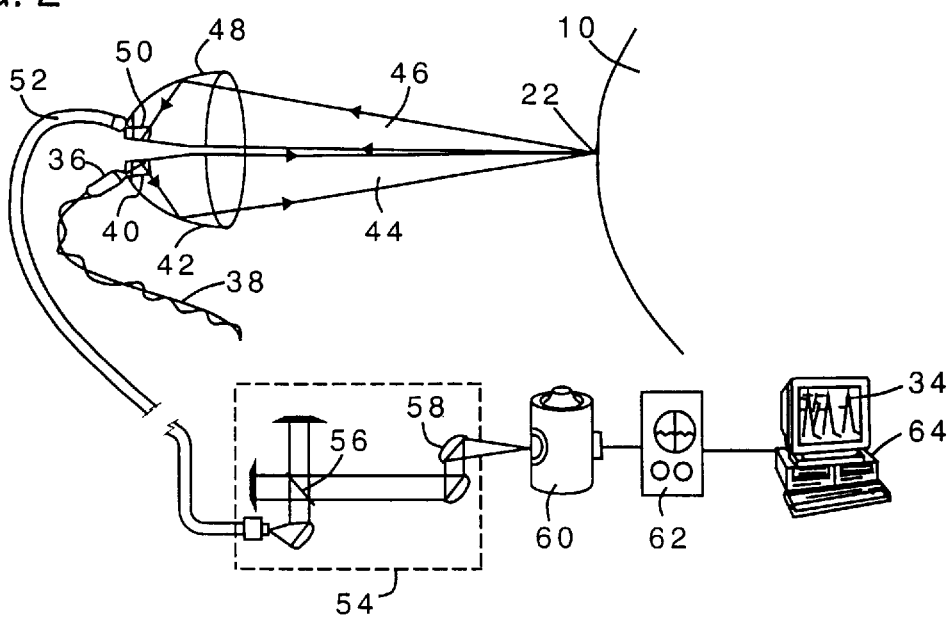

NON-CONTACT SPECTROSCOPY SYSTEM AND PROCESS

STATEMENT AS TO FEDERALLY SPONSORED RESEARCH

This invention was made with Government support under Contract No. F33615-92-C-5982 awarded by the Air Force. The Government has certain rights in this invention.

BACKGROUND OF THE INVENTION

This invention relates to the spectroscopic technology, and more particularly to technology for analyzing materials and material surfaces using reflectance absorption spectroscopy.

Spectroscopy is frequently employed in qualitative and quantitative analysis of materials. Infrared radiation detection techniques frequently provide advantages over spectroscopic techniques using radiation of shorter wavelengths, such as visible or ultraviolet radiation, as organic and biological materials have characteristics strong and relatively narrow unique identifying absorption peaks in the infrared region. Remote infrared spectroscopic monitoring using optical fibers is discussed, for example, in Stevenson, U.S. Reissue Pat. No. 33789, Bornstein et al., U.S. Pat. No. 5,070,243, Stevenson, U.S. Pat. No. 5,239,176, and Cook, U.S. Pat. No. 4,852,967.

The invention, in particular applications, enables rapid (multiscans per second) and remote, non contact determination of infrared spectra of large surface areas. An example of such applications is the scanning of the surface of an airplane prior to painting to determine if contaminants which may interfere with the painting process are on the surface of the airplane. In such an application, the system needs to be relatively tolerant of curved surfaces and irregularities such as rivets. The typical surface preparation treatment includes application of a phenolic paint stripper, followed by a rinse, detergent wash, a second rinse, sealing of surfaces with a silicone sealant, a second detergent wash and rinse, application of a skin brightener, further rinse, a chromic acid rinse and dry. The airplane surface is then masked and painted with material such as a self-priming topcoat (SPT) polyurethane. Adhesion of the paint will be affected by the presence of surface contamination; an adhesion of a second coating of paint will be affected by the "dryness" of each coating prior to the application of the next coating. If there is contamination or improper cure, the layer of paint will delaminate. For example, the area underneath the engine nacelle can be contaminated with fuel, lubricating fluid and hydraulic fluid.

Another cause for paint delamination is the incomplete cure of the silicone sealant which is used extensively on aircraft to protect cadmium plated rivets and faying edges from the skin brightener and chromic acid etch. If the sealant is not completely cured before the paint is applied, outgassing from the sealant occurs which results in paint delamination from those regions. The invention is also useful in monitoring chemical reactions such as paint cure.

In accordance with one aspect of the invention, there is provided a non-contact spectroscopy system that includes scanning head structure with transmitting optics for focusing radiation (that may be in the visible, ultraviolet or infrared range depending on the type of sample being analyzed) onto the surface of material to be analyzed, and receiving optics for collecting radiation reflected from the surface of the material and directing the reflected radiation onto optic fiber structure for transmission to spectroscopic analyzer apparatus.

In particular embodiments, the transmitting optics includes ellipsoid mirror structure to focus broadband infrared radiation from a source emitting radiation in the infrared (IR) wavelength range of about two microns to twenty microns onto a material surface located about one-half meter from the mirror. The receiving optics includes second ellipsoid mirror structure and redirection mirror structure for directing the reflected radiation onto an infrared transmitting optic fiber for transmission to a remotely located high resolution Fourier transform infrared (FTIR) spectrometer with scanning capabilities of about 100 scans per second. The spot size imaged on the surface is about one centimeter in diameter, and the high throughput and fast scanning capability of the FTIR spectrometer permits rapid raster scanning of surfaces so that large areas can be scanned at rates of about one half square meter per minute.

The optic fiber structure preferably has a length of at least one meter, a continuous core and continuous cladding over its entire length. In particular embodiments, the fiber core is of a chalcogenide glass such as arsenic, selenium tellurium, arsenic trifluoride, germanium selenium tellurium, or arsenic germanium selenium; a heavy metal fluoride glass such as zirconium, barium, lanthanum, aluminum, or sodium fluoride; fused silica or silicate glasses; or crystal material such as silver halide, thalium bromoiodide or cesium halide or sapphire. Preferably the core has a diameter of at least fifteen micrometers but less than one millimeter and a refractive index greater than 1.5. The fiber cladding is of composition similar to the core composition but has a lesser refractive index. The fiber may have a length of ten meters or more.

The system in particular embodiments includes scanning drive structure for moving the scanning head structure at a rate of at least ten scans per second over a scan length of at least 0.1 meter. In a particular embodiment, the drive structure is of the raster scan type, and the system further includes apparatus for generating an alignment radiation beam for impingement on the surface being analyzed to provide a visual indication of the particular region being analyzed.

In accordance with another aspect of the invention, there is provided a process in which a surface to be painted is scanned to obtain an infrared spectrum by a diffuse reflectance infrared technique which involves directing an IR beam at the sample surface, the beam being selectively absorbed by the sample surface so that the reflected bean contains IR spectral information concerning the surface characteristics and the reflected beam is analyzed.

In accordance with another aspect, there is provided a noncontact spectroscopy process for noncontact analysis of a sample that includes the steps of providing a radiation source, directing a beam of radiation from the source onto a surface of material to be analyzed, collecting radiation reflected from the surface, and applying the collected reflected radiation to optical fiber structure for transmission to analyzing apparatus. The process preferably includes the steps of providing scanning head structure with transmitting optics in the scanning head structure for directing radiation in the beam of radiation onto a surface of material to be analyzed that spaced from the scanning head structure, and receiving optics in the scanning head structure for collecting radiation reflected from the surface of the material, and moving the transmitting and receiving optics relative to the material to be analyzed in a scanning operation.

In accordance with another aspect, there is provided for use in a spectroscopy system, scanning head structure that includes optical fiber structure, transmitting optics for focusing broad band radiation onto the surface of material to be analyzed remote from the scanning head structure, and receiving optics for collecting radiation reflected from the surface of the material and directing the reflected radiation onto the optical fiber structure for transmission over the fiber structure to a remotely located spectroscopic analyzing apparatus.

Other features and advantages of the invention will be seen as the following description of particular embodiments progresses, in conjunction with the drawings, in which:

FIG. 1 is a diagrammatic view of an inspection system in accordance with the invention;

FIG. 2 is a diagrammatic view of an embodiment of a spectroscopy system suitable for use in the system shown in FIG. 1;

DESCRIPTION OF PARTICULAR EMBODIMENTS

Figure 3:
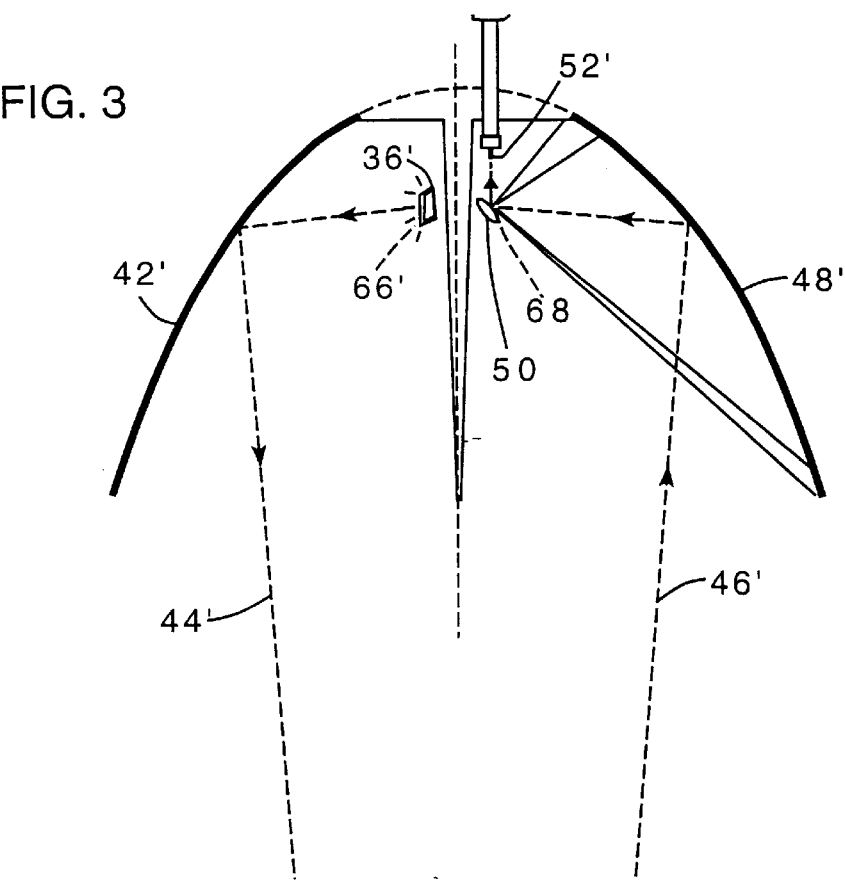
FIG. 3 is a diagrammatic view of portions of another embodiment of scanning head structure suitable for use in the system of FIG. 1.

Shown in FIG. 1 is aluminum aircraft surface 10 that is to be painted, surface 10 having rivets 12. An inspection system mounted on mobile support platform 14 includes gantry 16 that supports scanning head 18 with laser alignment structure 20 that provides indication 22 on aircraft surface 10 of the region being illuminated and robotic stepper 24 that provides a raster scan of the illuminated area at a rate of about 0.6 square meter per minute. Operator 26 controls the platform 14 and the gantry 16 through controls on pedestal 28 and scanning head and analyzer controls on pedestal 30. A spectrometer is housed in pedestal 32 and includes display 34.

A schematic diagram of the spectroscopy system is shown in FIG. 2. That system includes a light source 36 mounted in scanning head 18 and energized over lines 38. The output beam from source 36 is reflected by mirror 40 onto ellipsoidal reflector 42 for transmission in a beam 44 to region 22 of the aircraft surface 10 to be inspected. Radiation beam 46 reflected from surface 10 is focused by ellipsoidal reflector 48 and mirror 50 onto the end of a continuous clad optical transmission fiber 52 for transmission to FTIR spectrometer 54 of the Michelson interferometer type that includes beam splitter 56 and focusing mirrors 58. Coupled to the spectrometer 54 is MCT detector 60, analyzer 62 and output processor 64 that includes display 34.

Shown in FIG. 3 is a diagrammatic view of another embodiment of scanning head structure. The ellipsoidal reflectors 42', 48' are a modified Melles Griot reflector O2REMOO8 that has primary focal point 66 (at which source 36' is located) and primary focal point 68 (at which mirror 50' is located) that are each 17.2 millimeters from the vertex; a secondary focal point 414.6 millimeters from the vertex (at which the surface indication 26' is located); reflectors 42', 48' have heights of 65 millimeters each; the vertex aperture has a width of about 35 millimeters; and the mirror aperture has a width of 123.2 millimeters. The two ellipsoid mirrors 42', 48' share the same secondary focal point on surface 10', and the spot size imaged on surface 10' is about one centimeter in diameter. The reflector assembly may be movable by a suitable robotic stepper relative to the housing of the scanning head assembly in a raster scan mode for scanning at a rate of about 0.6 square meter per minute.

Disposed within the reflector assembly at the primary focal point of reflector 42' is globar source 36' which emits radiation in the IR wavelength region from about 2 microns to about 20 microns and is reflected in focused unmodulated beam 44' for impingement on surface 10' in an area of about one centimeter in diameter. The absorbed beam is reflected along path 46' for reflection by ellipsoidal reflector 48' and mirror 50' for transmission to the input end of optical fiber 52'. That fiber has a chalcogenide glass core of about 750 micrometers diameter and a cladding layer of chalcogenide glass of about 125 micrometers thickness. Optic fiber 52' has a numerical aperture of 0.5; the core has a glass transition temperature of 136° C., a thermal expansion coefficient of $23.6 \times 10^{-6}/°C.$, and a refractive index at 10.6 micrometers wavelength of 2.81; and the glass cladding has a glass transmission temperature of about 105° C. and a refractive index of about 2.18 at 10.6 micrometers.

Figure 4:
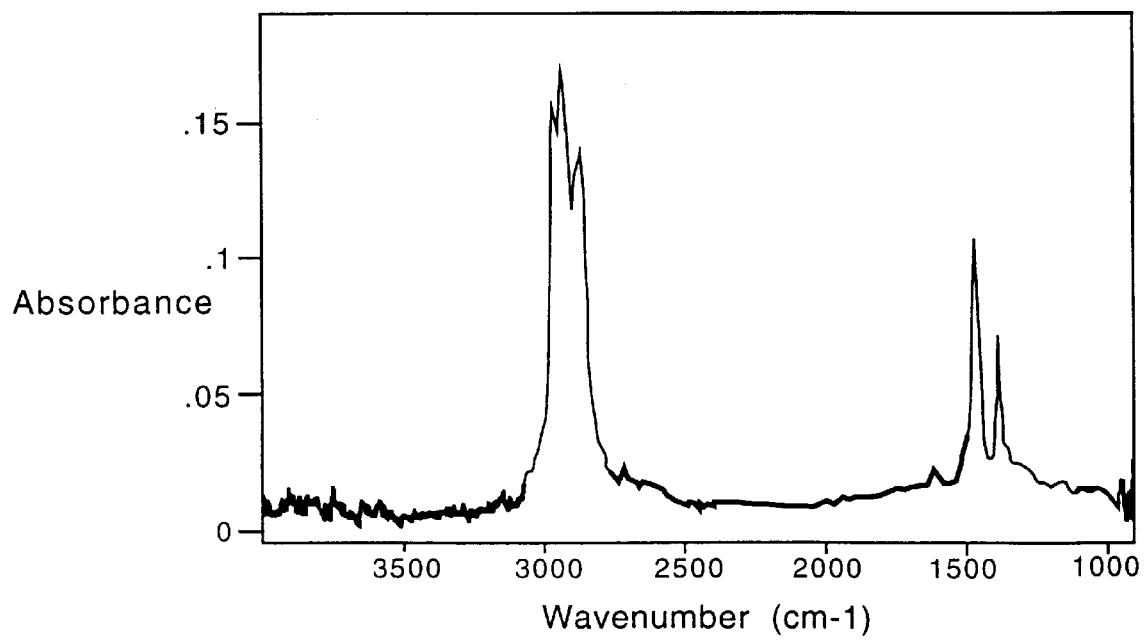
FIG. 4 is a single scan spectrum of jet fuel on an aluminum surface obtained in accordance with the invention.

FIG. 4 shows a single scan spectrum of JP8 jet fuel on an aircraft aluminum surface obtained with the optical system shown in FIG. 3.

Figure 5:
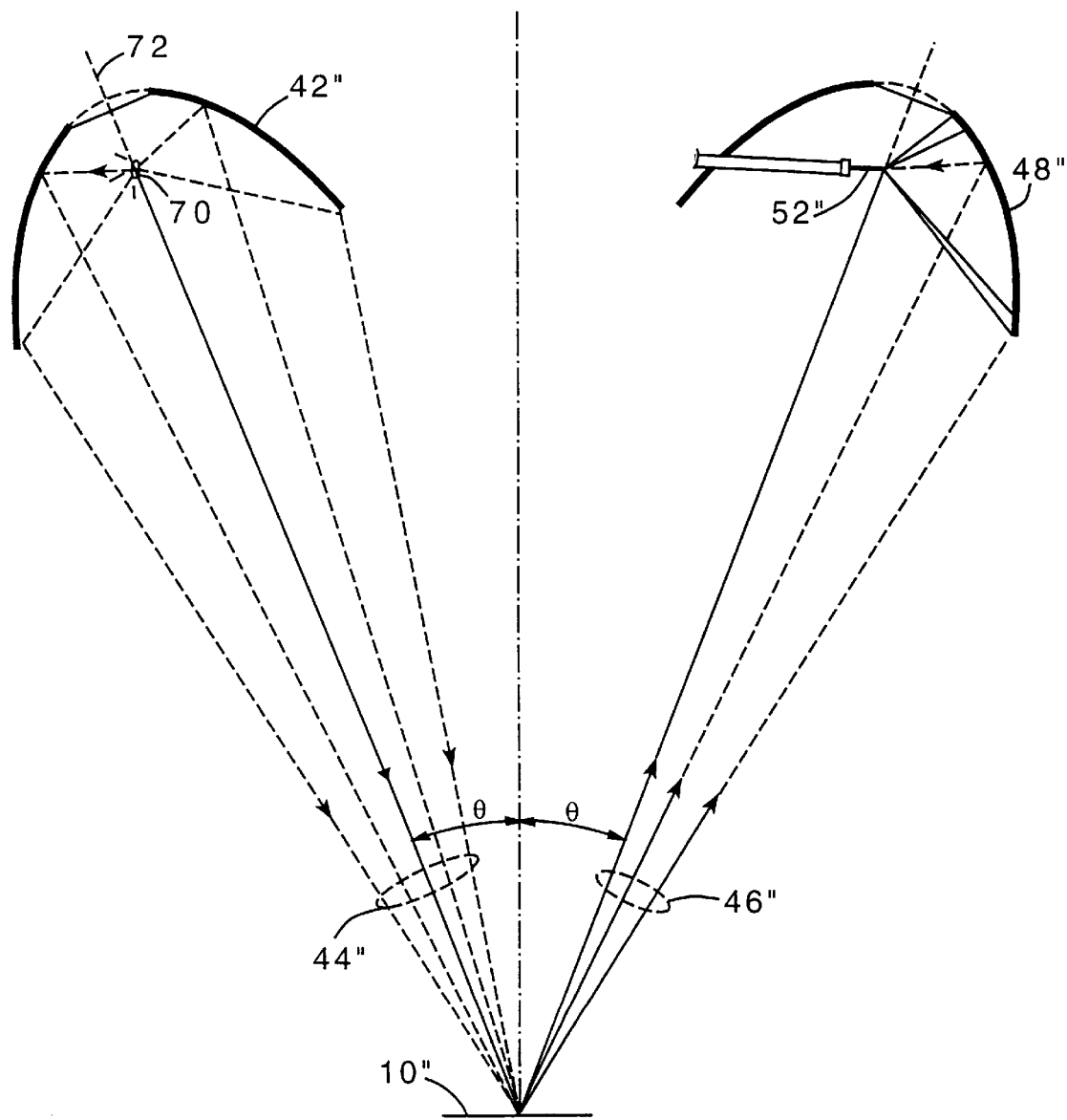
FIG. 5 is a diagrammatic view of another embodiment of mirror structure in accordance with the invention.

In another embodiment, shown in FIG. 5, mirror 70 is positioned at the primary focal point of ellipsoid reflector 42" for reflecting the unmodulated input radiation beam 74 onto the ellipsoid reflector 42" for transmission in beam 44" for absorption at surface 10" and reflection in beam 46" and focusing by ellipsoid reflector 48" onto optical fiber 52" for transmitting to an FTIR analyzer.

While particular embodiments of the invention have been shown and described, other embodiments will be apparent to those skilled in the art, therefore it is not intended that the invention be limited to the disclosed embodiments, or to details thereof, and departures may be made therefrom within the spirit and scope of the invention.

What is claimed is:

1. A spectroscopy system for non-contact analysis comprising analyzing apparatus, a source of radiation for generating a beam of radiation, scanning head structure comprising transmitting optics in said scanning head structure for directing radiation in said beam of radiation onto a surface of material to be analyzed that spaced from said scanning head structure, said transmitting optics focusing said beam of radiation in a region that is spaced at least 0.1 meter from said scanning head structure and that has a dimension of about one centimeter, and receiving optics in said scanning head structure for collecting radiation reflected from the surface of said material, and optical fiber structure having a core portion of less than one millimeter diameter for receiving said collected radiation and transmitting said collected radiation to said analyzing apparatus.

2. The system of claim 1 wherein said analyzing apparatus is of the Fourier transform type.

3. The system of claim 1 and further including drive apparatus for moving said transmitting and receiving optics relative to said material to be analyzed in a scanning operation.

4. The system of claim 1 wherein said fiber structure has a length of at least one meter.

5. The system of claim 4 wherein said radiation source is a broadband source of infrared radiation that emits radiation in the range of about two microns to twenty microns.

6. The system of claim 5 and further including scanning drive structure for moving said scanning head structure at a rate of at least 10 scans per second over a scan length of at least 0.1 meter.

7. The system of claim 1 wherein said optical fiber structure has a continuous core portion and continuous cladding over said core portion, said core and cladding having glass transition temperatures within about 100° C. of each other and thermal expansion coefficients within about $1 \times 10^{-6}$ per °C. of each other.

8. The system of claim 7 wherein said transmitting optics includes an ellipsoidal reflector and said receiving optics includes an ellipsoidal reflector and a supplemental reflector for directing radiation from said receiving optics ellipsoidal reflector into said core portion of said optical fiber structure.

9. The system of claim 7 wherein said core of said fiber is selected from the group consisting of chalcogenide glass, heavy metal fluoride glass, oxide glass and crystalline materials such as thalium bromohalides, cerium halides and silver halides.

10. The system of claim 9 wherein said fiber core has a length of at least one meter, a diameter in the range of 15–1000 micrometers and a refractive index greater than 1.5.

11. The system of claim 1 wherein each of said transmitting optics and said receiving optics includes an ellipsoidal reflector.

12. The system of claim 1 wherein said radiation source is a broadband source of infrared radiation that emits radiation in the range of about two microns to twenty microns.

13. The system of claim 1 and further including scanning drive structure for moving said scanning head structure at a rate of at least 10 scans per second over a scan length of at least 0.1 meter.

14. The system of claim 13 wherein said drive structure is of the raster scan type, and further including apparatus for generating an alignment radiation beam for impingement on the surface to provide a visual indication of the region being analyzed.

15. The system of claim 14 wherein said optical fiber structure has a length of at least one meter, a diameter in the range of 15–1000 micrometers and a refractive index greater than 1.5.

16. The system of claim 15 wherein said optical fiber structure has a continuous core portion and continuous cladding over said core portion throughout said transmission portion, said core and cladding having glass transition temperatures within about 100° C. of each other and thermal expansion coefficients within about $1 \times 10^{-6}$ per °C. of each other.

17. The system of claim 16 wherein said core of said fiber is selected from the group consisting of chalcogenide glass, heavy metal fluoride glass, oxide glass and crystalline materials such as thalium bromohalides, cerium halides and silver halides.

18. The system of claim 1 wherein said transmitting optics includes an ellipsoidal reflector and said receiving optics include an ellipsoidal reflector and a supplemental reflector for directing radiation from said receiving optics ellipsoidal reflector into said core portion of said optical fiber structure.

19. For use in a spectroscopy system, scanning head structure comprising a broadband source of infrared radiation that emits radiation in the range of about two microns to twenty microns, optical fiber structure, said fiber structure having a length of at least one meter, said optical fiber structure having a continuous core portion and continuous cladding over said core portion, said core portion and cladding having glass transition temperatures within about 100° C. of each other and thermal expansions coefficients within about $1 \times 10^{-6}$ per °C. of each other, and said core portion being selected from the group consisting of chalcogenide glass, heavy metal fluoride glass, oxide glass and polycrystalline or single crystal materials such as thalium bromohalides, cerium halides and silver halides, transmitting optics for focusing broad band radiation onto the surface of material to be analyzed remote from said scanning head structure, said transmitting optics including an ellipsoidal reflector for focusing said beam of radiation in a region that is spaced at least 0.1 meter from said scanning head structure and that has a dimension of about one centimeter, receiving optics for collecting radiation reflected from the surface of said material and directing said reflected radiation onto said optical fiber structure for transmission over said fiber structure to a remotely located spectroscopic analyzing apparatus said receiving optics including an ellipsoidal reflector and a supplemental reflector for directing radiation from said receiving optics ellipsoidal reflector into said core portion of said optical fiber structure; and drive apparatus for moving said transmitting and receiving optics relative to said material to be analyzed in a scanning operation.

\* \* \* \* \*